(12) United States Patent
Hossbach et al.

(10) Patent No.: US 10,979,697 B2
(45) Date of Patent: Apr. 13, 2021

(54) POST PROCESSING AND DISPLAYING A THREE-DIMENSIONAL ANGIOGRAPHY IMAGE DATA SET

(71) Applicant: Siemens Healthcare GmbH, Erlangen (DE)

(72) Inventors: Julian Hossbach, Erlangen (DE); Rainer Schneider, Erlangen (DE); Peter Speier, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/440,126

(22) Filed: Jun. 13, 2019

(65) Prior Publication Data

US 2019/0387217 A1 Dec. 19, 2019

(30) Foreign Application Priority Data

Jun. 13, 2018 (EP) .................... 18177503

(51) Int. Cl.
*H04N 13/351* (2018.01)
*H04N 13/344* (2018.01)
*G06T 11/00* (2006.01)

(52) U.S. Cl.
CPC ......... *H04N 13/344* (2018.05); *G06T 11/008* (2013.01); *H04N 13/351* (2018.05); *G06T 2210/41* (2013.01); *G06T 2211/404* (2013.01)

(58) Field of Classification Search
CPC .......... G06T 2210/41; G06T 2211/404; G06T 11/008; G06T 15/08; H04N 13/344;

(Continued)

(56) References Cited

U.S. PATENT DOCUMENTS

2007/0263915 A1* 11/2007 Mashiach ............ G06K 9/4638
382/130
2008/0212857 A1* 9/2008 Pfister ...................... G06T 5/50
382/130

(Continued)

FOREIGN PATENT DOCUMENTS

EP 2733947 A2 5/2014

OTHER PUBLICATIONS

Elliot K. Fishman et al, "Volume Rendering versus Maximum Intensity Projection in CT Angiography: What Works Best, When, and Why?", Radio Graphics, May-Jun. 2006, vol. 26, No. 3, pp. 905-923, EHB (Year: 2006).*

(Continued)

*Primary Examiner* — Dave Czekaj
*Assistant Examiner* — Berteau Joisil
(74) *Attorney, Agent, or Firm* — Schiff Hardin LLP

(57) ABSTRACT

A method for post processing and displaying a three-dimensional angiography image data set of a blood vessel tree of a patient, wherein two-dimensional display images are rendered from the angiography image data set and displayed, wherein two display images are rendered from the angiography image data set using viewing directions forming an angle suited for stereoscopic perception of the display images and both display images are simultaneously displayed on a display screen in a display presentation that causes each display image to be viewed by one eye of a person viewing the display screen.

15 Claims, 3 Drawing Sheets

(58) Field of Classification Search
CPC .... H04N 13/275; H04N 13/351; A61B 6/466; A61B 8/466; A61B 6/504
See application file for complete search history.

(56) References Cited

U.S. PATENT DOCUMENTS

| | | |
|---|---|---|
| 2014/0071254 A1 | 3/2014 | Gotman |
| 2014/0139526 A1 | 5/2014 | Kim et al. |
| 2018/0077409 A1* | 3/2018 | Heo ..................... H04N 13/122 |
| 2018/0124383 A1* | 5/2018 | Kroon ................. H04N 13/368 |

OTHER PUBLICATIONS

Volume Rendering versus Maximum Intensity Projection in CT Angiography: What Works Best, When, and Why Elliot K. Fishman et al.; Elliot K. Fishman et al., Volume Rendering versus Maximum Intensity Projection in CT Angiography: What Works Best, When, and Why, Radio Graphics, May-Jun. 2006, vol. 26, No. 3, pp. 905-923, EHB.

Ming-Yuen Chan et al: "MIP-Guided Vascular Image Visualization with Multi-Dimensional Transfer Function", Jan. 1, 2006 (Jan. 1, 2006), Advances in Computer Graphics Lecture Notes in Computer Science;;LNCS, Springer, Berlin, DE, pp. 372-384, XP019041351; ISBN: 978-3-540-35638-7; 2006.

Calhoun, Paul S. et al.: "Three-dimensional Volume Rendering of Spiral CT Data: Theory and Method"; in: RadioGraphics; vol. 19; No. 3; pp. 745-764; 1999.

* cited by examiner

POST PROCESSING AND DISPLAYING A THREE-DIMENSIONAL ANGIOGRAPHY IMAGE DATA SET

BACKGROUND

The present disclosure concerns a method for post processing and displaying a three-dimensional angiography image data set of a blood vessel tree of a patient, wherein two-dimensional display images are rendered from the angiography image data set and displayed. The disclosure also concerns a presentation device, a computer program and an electronically readable storage medium.

Angiography is a well-known medical imaging technique used to visualise blood vessels inside the body of a patient. Three-dimensional angiography image data sets may be acquired using X-ray imaging devices, wherein a contrast agent is injected into the patient to allow contrasting blood vessels with regard to other anatomical structures. It has, however, also been proposed to use magnetic resonance imaging (MRI) to image blood vessels of a patient, for example to diagnose stenosis, occlusions or aneurysms. In any case, the result of the acquisition is a three-dimensional angiography image data set describing an acquired part of the blood vessel tree of the patient which has to be visualised, in particular presented to a diagnosing/reviewing physician.

Rendering techniques are commonly used to calculate two-dimensional images which can be displayed as representations of a volumetric data set. Rendering techniques have also already been employed with regard to angiography. A widespread used variant of rendering in angiography is the so-called maximum intensity projection (MIP). In MIP, each voxel along a line from the viewer's eye or along parallel lines in a viewing direction through the volume of data is evaluated and the maximum voxel value is then used as the displayed value. MIP has proven to be particularly useful in creating angiographic display images from computed tomography and magnetic resonance image data sets. The usability of MIP as a rendering technique as well as variance and embodiments have been discussed across the literature in an extensive way. For example, it is referred to P. S. Calhoun et al., "Three-dimensional Volume Rendering of Spiral CGT Data: Theory and Method", RadioGraphics 19 (1999) 745-764, and Elliot K. Fishman et al., "Volume Rendering versus Maximum Intensity Projection in CT Angiography: What Works Best, When, and Why", RadioGraphics 26 (2006) 905-922. However, MIP has certain drawbacks, since this rendering technique does not incorporate the actual 3D relationship of the structures leading to a loss of information and the delineation of individual structures is aggravated through the overlaid high intensity voxels. More precisely, crossing and overlapping of vessel structures severely impair the ability for diagnosis and result in a cumbersome "browsing-technique" by the radiographer, i.e. stepping through the stack of slices forth and back trying to distinguish fine structures. This results in a significant lengthening of the review workflow for three-dimensional angiography image data sets. Many of these or comparable problems also apply to other volume rendering techniques.

To overcome these problems, some methods have already been proposed in the state of the art. For example, as display images, so-called depth-enhanced MIPs could be used, which, however, requires a second ray casting and is consequently computationally complex. Using other volumetric rendering techniques as alternative visualisations often leads to less detailed display images as a result of a more complex computation. Additionally, perspective projections can lead to an unsteady and high frequent visualisation of structures farther away from the viewpoint. It has also been proposed to use so-called 3D monitors, which, however, require a special environment and are very expensive. Furthermore, such 3D monitors are influenced by ambient light. In another approach, a sophisticated visualisation of depth information, e.g. by using colors, has been proposed, which, however, may be difficult to interpret.

To facilitate the depth interpretation of rendered display images, it has also been proposed to render up to three display images, in particular using maximum intensity projection, having orthogonal image planes, which are simultaneously displayed. This visualisation, however, requires a high degree of spatial sense on the side of the user.

SUMMARY

It is thus an object of the present disclosure to provide a method for presenting a three-dimensional angiography image data set in a computational simple way, in particular in real time, which provides a better image quality and better interpretation.

This object is achieved by providing a method according to claim 1, a presentation device according to claim 11, a computer program according to claim 13 and an electronically readable storage medium according to claim 14. Advantageous embodiments are described in the dependent claims.

In a method as initially described for presenting a three-dimensional angiography image data set of a blood vessel tree of a patient, two display images are rendered from the angiography image data set using viewing directions forming an angle suited for stereoscopic perception of the display images and both display images are simultaneously displayed on a display device such that each display image is displayed to one eye of a user.

It is thus proposed to define a new sort of rendering instructions in combination with a new way of presenting the resulting display images. Two display images along different viewing directions, which form a small angle, for example smaller than 20°, preferably smaller than 10°, are rendered and a display device is used which enables presenting a display image for each eye respectively and independently. By addressing each eye with slightly off display images, a stereoscopic perception of the display images is enabled. That is, using an angle preferably smaller than 10° makes the images suitable for stereoscopic viewing.

This stereoscopic presentation of rendering results, in particular maximum intensity projections, leads to an improved three-dimensional perception of the structures in the blood vessel tree imaged, so that in particular fine structures can be better differentiated so that diagnosis is improved. While, according to the state of the art, the user reviewing the three-dimensional angiography image data set had to switch between different display images, in particular scroll through stacks of rendered display images and/or manually choose other viewing directions to get a feeling of the three-dimensional structure modelled by the angiography image data set, the workflow can, according to the present disclosure, be accelerated by avoiding cumbersome browsing techniques. The simplicity of the rendering instructions needed, in particular in the case of maximum intensity projections, allow very fast, in particular real-time, computation of the display images. The depth perception enabled by the present disclosure allows analyzing of overlapping structures in an appealing and intuitive presentation.

It has further been shown that such a stereoscopic display reduces the perception of noise present in the angiography image data set, since the noisy structures may appear only in one of the display images. In a particularly preferred embodiment, parallel rendering is used for determining the display images, that is, the rays do not emanate from a single viewpoint, but are chosen to run parallel. Using such a parallel projection additionally reduces noise and the complexity of the computation. The size perpetuation of parallel rendering/parallel projections prevents structures further away from the image plane from appearing smaller, which would lead to a noisy image perception.

If, in particular, maximum intensity projection along parallel rays is used, a very low complexity of the computation is given, reducing computational demand and enabling real-time applications.

In a preferred embodiment, the angiography image data set is divided into slices along a slicing direction, wherein the display images are calculated for at least one of the slices. This technique is, in principal, already known from the state of the art and has been called "thin MIP". In this technique, the volume covered by the angiography image data set is subdivided into thin slices for every view point and the so-called thin MIPs are rendered for every slice. If display images only rendered from one slice are displayed, the presentation also only refers to this slice. In this manner, structures of interest, for example the vessel of interest, can be reviewed independently and allocation of image data to depths and structures can be facilitated.

In an especially preferred embodiment, base images for base slices of a smallest allowable slice thickness are pre-calculated and display images for slices comprising multiple base slices are determined by combining the base images for the corresponding base slices. This initial pre-computation of very thin MIPs per viewing direction is advantageous, since the dynamic calculation of display images for thicker slices can be reduced to a simple maximum projection of the corresponding stack of base slices without the computational need of further parallel maximum intensity projections. If a slice chosen for a display, for example based on user input, corresponds to one single base slice, the corresponding base images can be used as a display images.

Preferably, display images for multiple slices are determined by assigning different colors to each slice and combining the respective slice images. In this manner, the visualisation of depth information can be further improved by using a predefined coloring, for example a color gradient for slices covered. Such a color gradient may, for example, range from blue to red for structures originating from slices further away from the image plane and closer to the image plane, respectively. In particular, the base slices, in particular the thin MIPs, can be used for assigning colors. This results in less computational demand than by using so-called depth-enhanced MIPs. The depth perception provided by the present disclosure also allows better interpretation of colors.

In preferred embodiments, the angle between the adjacent viewing directions is smaller than 20°, in particular smaller than 10°, and/or chosen automatically depending on a distance between the eyes of the user and/or a radius of a circle or sphere surrounding the blood vessel tree in the angiography image data set, on which the imaging planes of the display images are placed, and/or based on a user input. In most embodiments, the angle will be chosen empirically, for example, based on tests performed by users. For example, a suitable angle may be 4 to 6°, in particular 5°. Suitable values for the angle and how to choose them may also be taken from experience regarding other stereoscopic visualisation techniques. Preferably, the angle is automatically chosen and/or predetermined. It is, however, also possible to let the user choose a suitable angle, for example by providing an input means regarding this parameter.

Generally, to define image planes and/or viewing directions, that is, the rendering geometry, consistently, it may be provided that a circle or sphere of a certain radius around the centre of the blood vessel tree in the angiography image data set may be defined such that the centre positions of the respective imaging planes of the display images form a regular grid on the circle/sphere and such that each viewing direction (passing from the centre position of the image plane through the centre of the circle/sphere) has at least one neighbouring/adjacent further viewing direction spaced by the angle. The radius and the angle also define the eye or viewpoint distance, that is, the distance between centre positions of the image planes, which influences the overall size perception. The two display images to be at least computed are rendered with shifted viewpoints, i.e. centres of their image planes, on the circular or spherical shape having the defined radius, facing towards the centre of the circle/sphere. Arranging the selectable and/or pre-calculated display images or, more precisely, the centres of their image planes, in a regular grid on the circle or sphere results in each display image having at least one partner with a viewing direction rotated by the angle. Two such display images whose viewing directions are rotated relative to each other by the angle form a pair which can be displayed simultaneously on the display device and enable the stereoscopic visualisation/perception.

Therefore, in preferred embodiments, display images for more than two viewing directions are calculated, each adjacent pair of which drawing the angle, wherein a pair of display images for display having adjacent viewing directions is chosen based on user input. The more than two display images may preferably be pre-calculated as a set of display images. Alternatively, the two initially needed display images may be calculated and additional images may then be calculated on demand. The centres of the image planes of these display images may, as described, in particular lie on a regular grid on the surface of a circle or sphere defined around the blood vessel tree in the angiography image data set.

Preferably, the pairs of viewing directions cover at least a semi-circle or semi-sphere of possible image plane positions on a circle or sphere surrounding the blood vessel tree in the angiography image data set. When using parallel maximum intensity projections, the display images of the remaining semi-circle and/or semi-sphere correspond to already known display images.

A mean viewing direction can be described as the angle bisector of the viewing directions of the two simultaneously displayed display images. When a user input comprises changing the mean viewing direction to a neighbouring mean viewing direction, the previous display image lying in the direction of the change is moved to be displayed to the other eye and a new display image having a viewing direction adjacent to the moved display image in the direction of change is added to the display images currently displayed. In other words, rotation is performed by switching to the neighbouring pair of display images.

It is noted that any known display manipulation technique like, for example, value windowing and/or zoom, may, of course, also be implemented in the inventive method. Input means for receiving user input may, for example, comprise a keyboard, a game controller, a gesture recognition device, a voice command recognition device and/or other devices. Rotation may, as described, be performed by switching to the neighbouring pair of display images.

In an especially preferred embodiment, stereoscopic glasses comprising a display for each eye of a user are used as the display device, wherein one display image is displayed on each display of the stereoscopic glasses. In particular, smart glasses may be used as the stereoscopic glasses. In the present disclosure, head-mounted displays or equivalent devices are preferably used as display device, in particular stereoscopic glasses. Any known glasses allowing independent control of the displays associated with each eye may be used, for example, virtual reality glasses, augmented reality glasses and/or mixed reality glasses. Advantageously, environmental influences may be cancelled by isolatedly displaying the display images using a head-mounted display. It is noted that such head-mounted displays, in particular stereoscopic glasses, are available at low cost, which is an additional advantage of the present disclosure.

The disclosure further concerns a presentation device for post processing and displaying a three-dimensional angiography image data set of a blood vessel tree of a patient, comprising a display device and a control device having
  a rendering unit for rendering two-dimensional display images from the angiography image data set, wherein two display images are rendered from the angiography image data set using viewing directions forming an angle suited for stereoscopic perception of the display images, and
  a display unit for displaying both display images simultaneously on the display device such that each display image is displayed to one eye of a user. Preferably, the presentation device may also comprise at least one input means for receiving user input, for example relating to choosing a new mean view direction and the like.

All features and remarks regarding the method according to the disclosure may also be applied correspondingly to the inventive presentation device. In particular, the control device of the presentation device may be adapted to perform a method according to the disclosure.

A computer program according to the disclosure can, for example, be loaded into a memory means of a control device of a presentation device and comprises program means to perform the steps of a method according to the disclosure if the computer program is executed in the control device of the presentation device, in particular by a processor of the control device. The computer program may be stored on an electronically readable storage medium according to the disclosure, which thus comprises electronically readable control information stored thereon, which comprises at least a computer program according to the disclosure and is configured such that, when the electronically readable storage medium is used in a control device of a presentation device, a method according to the disclosure is performed. The storage medium may be a non-transient storage medium, in particular a CD-ROM.

BRIEF DESCRIPTION OF THE DRAWINGS

Further details and advantages of the present disclosure become apparent from the following description of detailed embodiments taken in conjunction with the drawings, in which.

DETAILED DESCRIPTION

The following embodiments relate exemplarily to three-dimensional magnetic resonance angiography image data sets acquired with a magnetic resonance device, but can, however, also be applied to other imaging techniques as a source of the three-dimensional data. The embodiments described herein describe visualization, that is presentation, of the blood vessel tree described by the angiography image data set from at least one mean viewing direction, wherein, in general, two display images for simultaneous display are computed by parallel maximum intensity projection (MIP) as a rendering technique. The viewing directions of the pair of display images to be simultaneously displayed, each to another eye of a user, draw an angle smaller than 10°, for example 5°, which is suitable for stereoscopic viewing.

Figure 1:
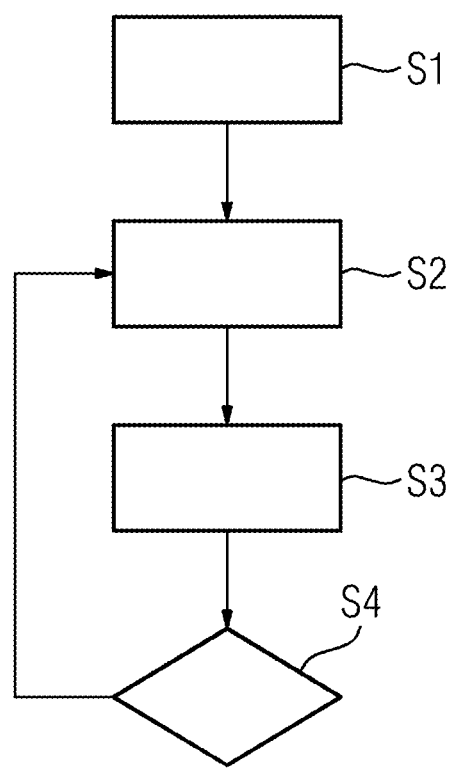
FIG. 1 shows a general flow chart of embodiments of the present disclosure.

A flowchart of an embodiment of the method according to the disclosure is shown in FIG. 1. In a step S1, rendering geometries for rendering the display images are defined. For two display images, this is further explained with respect to FIG. 2.

Figure 2:
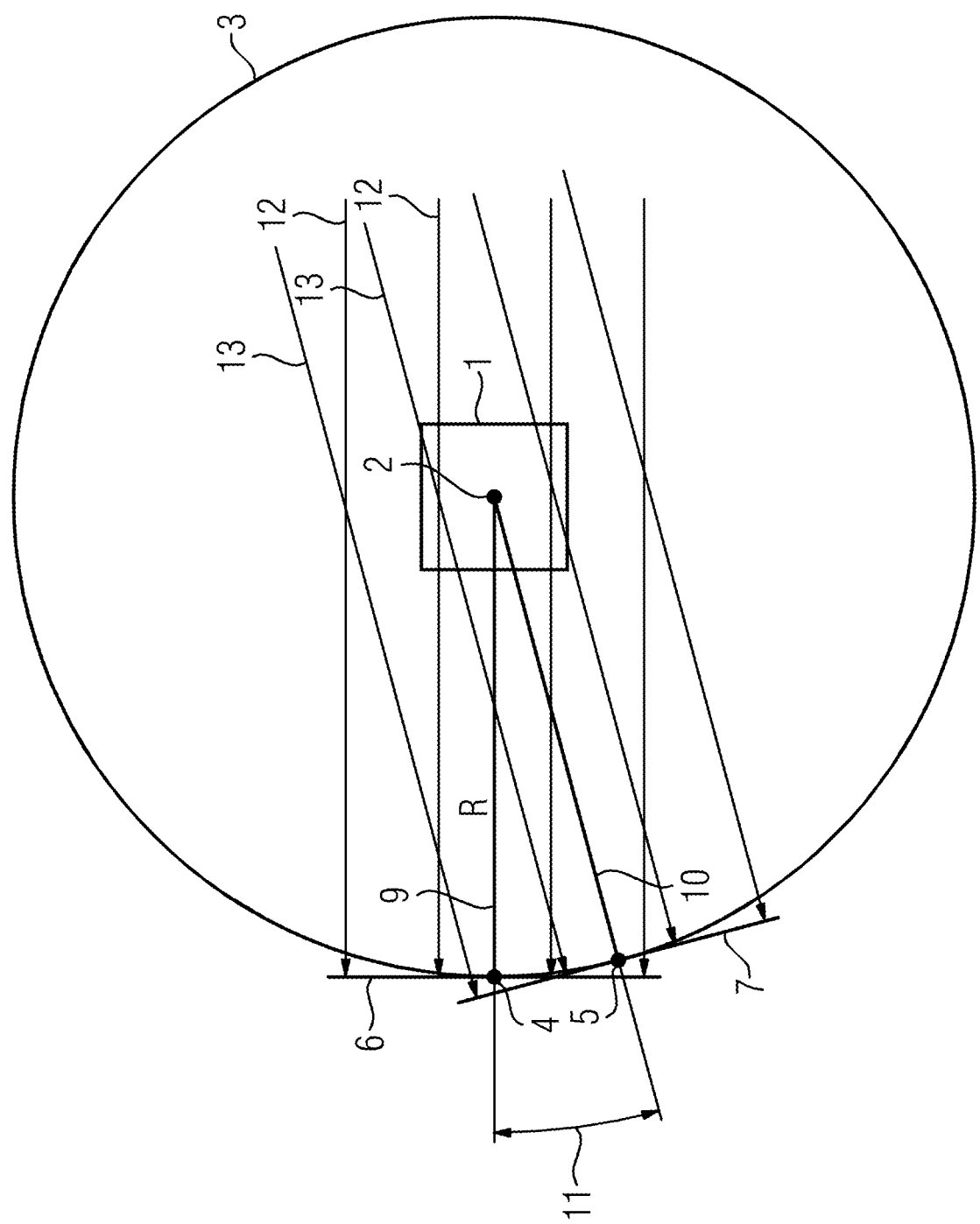
FIG. 2 shows a possible definition of rendering geometries.

In FIG. 2, the volume 1 covered by the angiography image data set and containing the depiction of the blood vessel tree of the patient, in turn comprises a centre 2 which may be the centre of the acquired part of the blood vessel tree or another well-defined point in the volume 1, for instance its centre. Surrounding the centre point 2 and therefore the volume 1, a circle or sphere 3 with radius A is defined. On the surface of this circle or sphere 3, centre points 4, 5 of image planes 6, 7 may be defined according to viewing directions 9, 10 connecting the centre 2 and the respective centre points 4, 5 of the image planes 6, 7. The viewing directions 9, 10 are defined to draw an angle 11 between them, which may, as already discussed, for example be 5°. The radius R and the angle 11 define the eye or view point distance, that is, the distance between the centre points 4 and 5.

For the image planes 6, 7, parallel maximum intensity projection may now be performed in a step S2 to yield two display images suitable for stereoscopic vision, as indicated by the respective parallel rays 12, 13.

While the method according to the disclosure can already be performed by defining these two rendering geometries and render two display images regarding the volume 1, advantageous embodiments use more than two viewing directions 9, 10 whose respective centre points 4, 5 are arranged in a regular grid on the surface of the circle or sphere 3. It suffices to cover a semi-circle or semi-sphere, that is, 180°, by this grid, since maximum intensity projections for the remaining areas correspond to these of the semi-circle or semi-sphere due to using parallel maximum intensity projection as a rendering technique.

Display images for all viewing directions 9, 10 corresponding to centre points 4, 5 on the regular grid may be pre-calculated, however, in a preferred embodiment, the advantages of so-called thin MIPs are used. In such embodiments, the volume 1 is subdivided into thin slices and maximum intensity projections are pre-calculated for each viewing direction 9, 10 and each of these base slices. For a thin slice itself, the corresponding base maximum intensity projection (as a base image) may immediately be used for display, for thicker slices comprising multiple base slices, display images, that is, again maximum intensity projections, may be calculated by a simple maximum projection of the respective stacks, such that way less computing power is necessary. Using such base images, in this embodiment base maximum intensity projections, for base slices has the further advantage that depth information may be encoded in display images by assigning different colors to different base slices covered by a thicker slice. For example, a predefined color gradient may be used.

As already explained, in step S2, at least two maximum intensity projections with shifted viewpoints (centre positions 4, 5) are determined, wherein due to the regular grid, each display image computed this way has at least one partner whose viewing direction 9, 10 is shifted by the angle 11. One of these pairs, selected or defined by user input or a default starting information, is then displayed simultaneously using a display device in step S3. As a display device, a head-mounted display, in particular stereoscopic glasses, are used. Each of the pair of display images is displayed to only one eye of the user, such that a stereoscopic perception of the display images results.

In a step S4, user input regarding a rotation of the mean viewing direction may be received. If such user input is received, rotation may be enabled by switching to a neighbouring pair of viewing directions 9, 10 (such that one viewing direction is kept) and thus display images in the regular grid. When switching to a neighbouring pair of viewing directions, one display image in the switching direction may be kept and moved to be displayed to the other eye. Only the display image for the next viewing direction 9,10 in the direction of change needs to be calculated, or, if it is already pre-calculated, retrieved. A rotation around the full volume 1 can be achieved by successively displaying neighbouring pairs of display images, each having viewing directions 9, 10 drawing the angle 11.

Other presentation manipulation techniques, like windowing, zoom, padding and the like, can also be included. Using zoom and padding may also have the benefit that barrel correction of lenses is no longer required if only inner areas not subject to distortion are automatically and/or manually chosen for display.

User input can be received from a corresponding input means, for example a keyboard, a joystick or other game controller, a gesture recognition device, a voice command recognition device, a mouse and the like.

Figure 3:
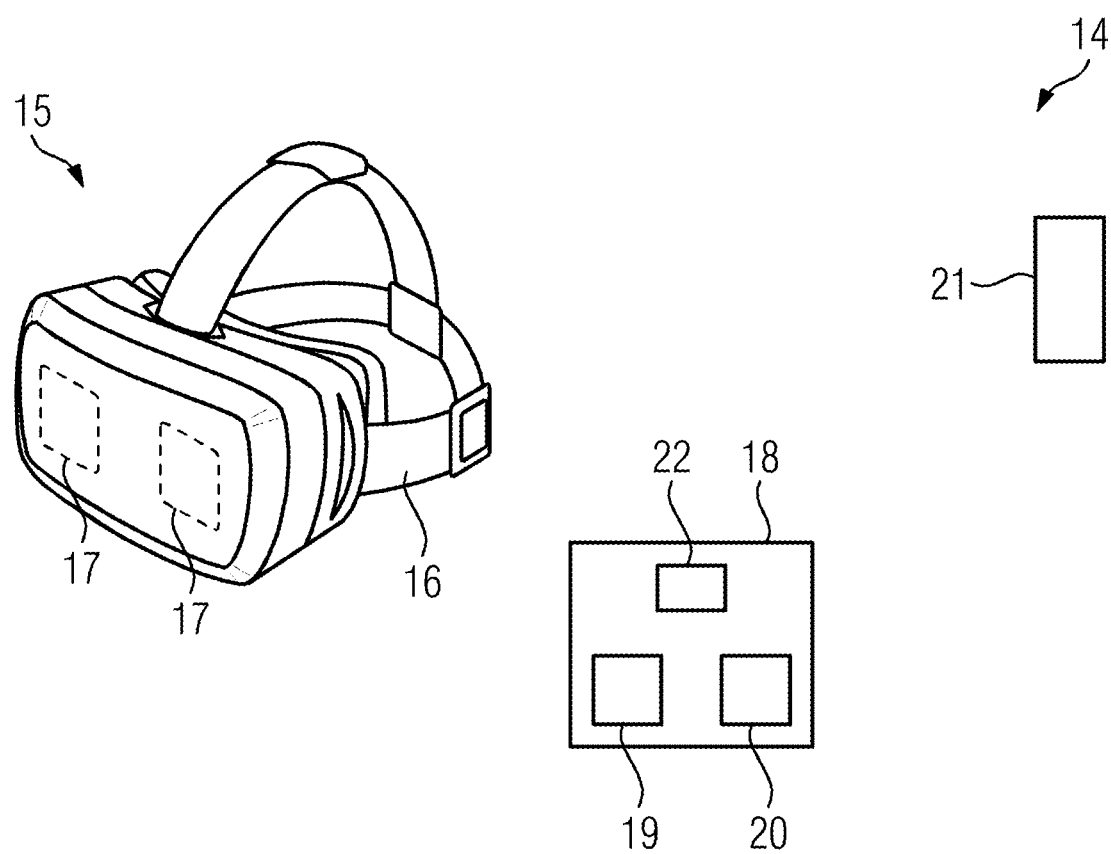
FIG. 3 shows a presentation device according to the disclosure.

FIG. 3 shows a presentation device 14 according to the present disclosure. The presentation device 14 comprises a display device 15, in this embodiment a head mounted display in form of stereoscopic virtual reality glasses 16. The glasses 16 comprise displays 17 for each eye of a user, which are only indicated in FIG. 3. On each of those displays 17, one display image of the pair whose viewing directions 9, 10 draw the angle 11 may be displayed to provide stereoscopic perception of the acquired part of the blood vessel tree described by the angiography image data set.

The presentation device 14 further comprises a control device 18, which is configured to perform a method according to the disclosure. To this end, the control device 18 comprises at least a rendering unit 19 and a display unit 20 for controlling the display device 15 to display one display image of a pair on each display 17, respectively.

The control device 18 may, of course, comprise further units, for example a unit for interpreting user input received by an input means 21, which may for example be a handheld device, a keyboard, a game controller or the like. The control device may be integrated into the display device 15, but preferably communicates wirelessly with the display device 15.

The control device 18, which comprises at least one processor (not shown), in this embodiment also comprises a memory means 22 in which, for example, base images for different base slices and viewing directions 9, 10 may be stored.

Although the present disclosure has been described in detail with reference to the preferred embodiment, the present disclosure is not limited by the disclosed examples from which the skilled person is able to derive other variations without departing from the scope of the disclosure.

The invention claimed is:

1. A method for post processing and displaying a three-dimensional angiography image data set of a blood vessel tree of a patient, the method comprising:
    rendering two-dimensional display images from the angiography image data set using viewing directions forming an angle suited for stereoscopic perception of the display images, wherein the angle between adjacent viewing directions is chosen automatically depending on a radius of a circle or sphere surrounding the blood vessel tree in the angiography image data set, on which the imaging planes of the image are placed; and
    displaying both display images simultaneously on a display screen in a display presentation that causes each display image to be viewed by one eye of a person viewing the display screen.

2. The method according to claim 1, further comprising:
    determining the display images using parallel rendering and/or maximum intensity projection.

3. The method according to claim 1, further comprising:
    dividing the angiography image data set into slices along a slicing direction; and
    calculating the display images for at least one of the slices.

4. The method according to claim 3, further comprising:
    precalculating base images for base slices of a smallest allowable slice thickness; and
    determining display images for slices comprising multiple base slices by combining the base images for the corresponding base slices.

5. The method according to claim 3, further comprising:
    determining display images for multiple slices by assigning different colors to each slice and combining the respective slice images.

6. The method according to claim 1, wherein the angle between the adjacent viewing directions is smaller than 20°.

7. The method according to claim 1, wherein the angle between the adjacent viewing directions is smaller than 10°.

8. The method according to claim 1, wherein the angle between the adjacent viewing directions is chosen automatically depending on a distance between the eyes of the user.

9. The method according to claim 1, wherein the angle between the adjacent viewing directions is based on a user input.

10. The method according to claim 1, further comprising:
    calculating display images for more than two viewing directions, each adjacent pair of which forms the angle; and
    choosing a pair of display images having adjacent viewing directions based on user input.

11. The method according to claim 10, wherein the pairs of viewing directions cover at least a semi-circle or semi-sphere of possible image plane positions on a circle or sphere surrounding the blood vessel tree in the angiography image data set.

12. The method according to claim 1, wherein stereoscopic glasses comprising a display for each eye of a person are used as the display screen, and one display image is displayed on each display of the stereoscopic glasses.

13. The method according to claim 12, wherein smart-glasses are used as the stereoscopic glasses.

14. A controller of a display presentation having a display screen and for post processing and displaying a three-dimensional angiography image data set of a blood vessel tree of a patient, the controller comprising:

a renderer configured to render two-dimensional display images from the angiography image data set using viewing directions forming an angle suited for stereoscopic perception of the display images; and a display configured to display both display images simultaneously on the display screen of the display presentation that causes each display image to be viewed by one eye of a person viewing the display screen, wherein the controller is adapted to perform the method of claim 1, and is also adapted to:

divide the angiography image data set into slices along a slicing direction;

calculate the display images for at least one of the slices;

precalculate base images for base slices of a smallest allowable slice thickness; and determine display images for slices comprising multiple base slices by combining the base images for the corresponding base slices.

15. A non-transitory computer readable medium comprising a computer program, which performs the method according to claim 1 when the computer program is executed on a controller of a presenter, and wherein the method further comprises:

calculating display images for more than two viewing directions, each adjacent pair of which forms the angle; and choosing a pair of display images having adjacent viewing directions based on user input, wherein the pairs of viewing directions cover at least a semi-circle or semi-sphere of possible image plane positions on a circle or a sphere surrounding the blood vessel tree in the angiography image data set.

* * * * *